(12) United States Patent
Mueller

(10) Patent No.: US 9,098,987 B2
(45) Date of Patent: Aug. 4, 2015

(54) SMOKE DETECTOR

(71) Applicant: SCHAKO KLIMA LUFT Ferdinand Schad KG, Kolbingen (DE)

(72) Inventor: Rainer Mueller, Kolbingen (DE)

(73) Assignee: SCHAKO KLIMA LUFT Ferdinand Schad KG, Kolbingen (DE)

( * ) Notice: Subject to any disclaimer, the term of this patent is extended or adjusted under 35 U.S.C. 154(b) by 0 days.

(21) Appl. No.: 13/950,774

(22) Filed: Jul. 25, 2013

(65) Prior Publication Data

US 2014/0226162 A1    Aug. 14, 2014

(30) Foreign Application Priority Data

Feb. 8, 2013  (DE) .......................... 10 2013 101 280

(51) Int. Cl.
*G01N 21/00* (2006.01)
*G08B 17/103* (2006.01)
*G01N 21/59* (2006.01)
*G01N 21/53* (2006.01)

(52) U.S. Cl.
CPC .............. *G08B 17/103* (2013.01); *G01N 21/53* (2013.01); *G01N 21/59* (2013.01)

(58) Field of Classification Search
USPC .......... 356/437–439, 337–343; 250/573–575, 250/200; 340/630, 628
See application file for complete search history.

(56) References Cited

U.S. PATENT DOCUMENTS

| | | | |
|---|---|---|---|
| 6,225,910 B1 * | 5/2001 | Kadwell et al. | 340/630 |
| 2009/0256714 A1 * | 10/2009 | Loepfe et al. | 340/628 |
| 2013/0201479 A1 * | 8/2013 | Vollenweider | 356/343 |

FOREIGN PATENT DOCUMENTS

DE    19951403 A1    5/2001

\* cited by examiner

*Primary Examiner* — Tri T Ton
(74) *Attorney, Agent, or Firm* — Bachman & LaPointe, P.C.

(57) ABSTRACT

A smoke detector with a transmitter (4) for a radiation that can be detected by a receiver (5), the transmitter (4) and the receiver (5) are to be assigned a monitored region (11).

1 Claim, 1 Drawing Sheet

SMOKE DETECTOR

BACKGROUND OF THE INVENTION

The present invention relates to a smoke detector with a transmitter for a radiation that can be detected by a receiver.

Smoke detectors are known and on the market in various forms and configurations. The present invention relates in particular to smoke detectors that are flush with a ceiling, as described in particular in DE 199 51 403 B4. There, a radiation is emitted from a transmitter in a ceiling through a covering into free space, this radiation is reflected at least partly by the smoke and is registered by a receiver behind the covering. A control program detects a deviation of the reflection and analyzes whether the deviation originates from smoke or from a foreign body, a multitude of detection processes being carried out within a unit of time and an alarm only being set off when a specific number of detection processes are positive in succession and, to distinguish between smoke and foreign bodies, a distinction is established between a continuous increase in the reflection, as in the case of smoke, and an abrupt increase in the reflection, as in the case of a foreign body. Furthermore, for the self-monitoring of this smoke detector, the transmitter is assigned a receiver of its own for receiving a radiation reflected from the covering and the receiver is assigned a transmitter of its own in front of the covering.

The present invention addresses the problem of further improving such smoke detectors and, in particular, monitoring better the surroundings of the smoke detector itself.

SUMMARY OF THE INVENTION

The solution to the problem is obtained by the transmitter and receiver being assigned a separately monitored region.

The essence of the present invention lies in the self-monitoring of the smoke detector in the form of a further movement detecting device. For this reason there is provided for the monitored region a monitoring transmitter of its own with a radiation of its own, which is assigned at least one monitoring receiver of this radiation. These components are preferably located in corresponding openings in an end plate, according to the invention the opening for the transmitter being specially designed. This opening is intended to be formed at least partially in the shape of a funnel, so that the radiation is not introduced way down into the room in one beam, but as it were in the manner of a balloon or sheet. This monitoring consequently serves in particular for monitoring the space around the smoke detector. For example, it is also established whether the smoke detector is correctly placed, for example is not over a cupboard. For example, it is also established whether a cupboard or the like is pushed in front of the smoke detector.

It is particularly preferred if the monitoring transmitter itself is located in a cylindrical part of the opening, while this cylindrical part is adjoined by a cross-sectionally elliptical funnel. This allows the radiation to be concentrated in the manner of a sheet, as mentioned above, which contributes to a considerable improvement in the detection of movements.

The end plate is preferably one of the central parts of the smoke detector according to the invention; a second part is a control plate, which is assigned to the end plate and in which the corresponding electronic circuit elements are located. The end plate itself receives not only the monitoring transmitter and the at least one monitoring receiver but also the aforementioned transmitter and receiver known from the prior art for monitoring smoke in a room. This arrangement allows the entire smoke detector to be kept very flat, which makes fitting flush with a ceiling possible without a detection chamber protruding from the ceiling and without a labyrinth of light. All of the transmitters and receivers are arranged on one side of the end plate. The end plate with the correspondingly aligned openings or bores then makes it possible for the corresponding radiations to be emitted and received correctly.

BRIEF DESCRIPTION OF THE DRAWINGS

Further advantages, features and details of the invention emerge from the following description of preferred exemplary embodiments and on the basis of the drawing, in which.

DETAILED DESCRIPTION

Figure 2:
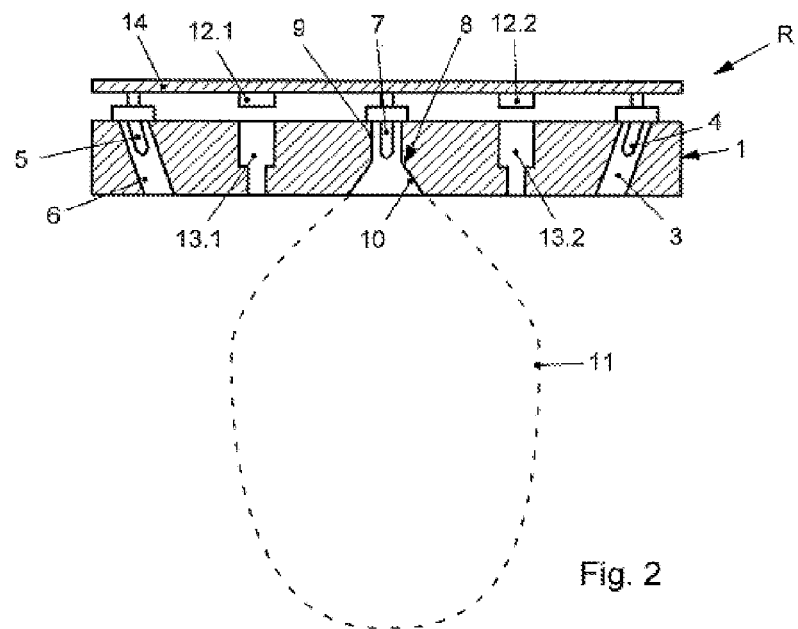
FIG. 2 shows a cross section through the smoke detector according to FIG. 1 along line II-II.
Figure 1:
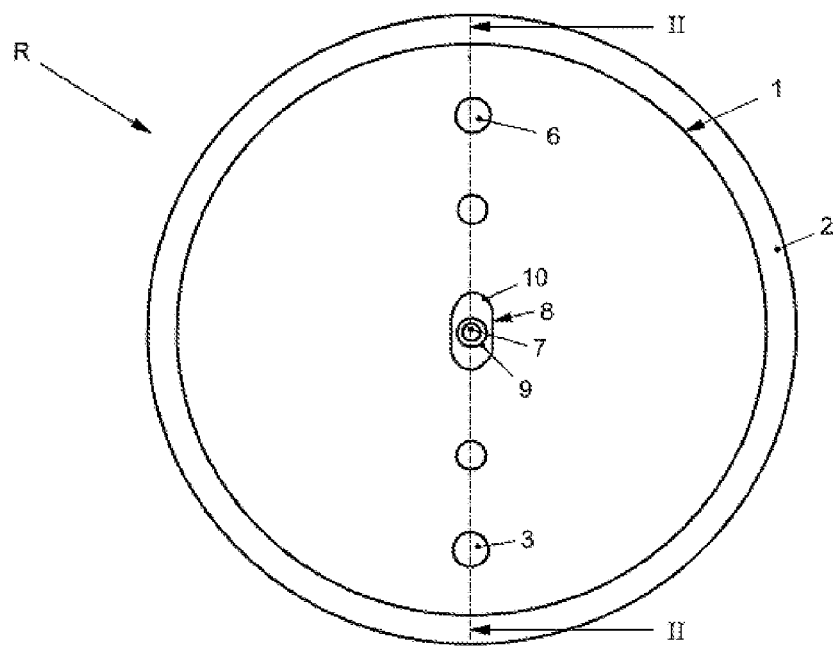
FIG. 1 shows a plan view of a smoke detector according to the invention.

According to FIG. 1, an end plate 1 with a side frame 2 of a smoke detector R according to the invention is shown. Various bores can be seen in the end plate 1. One bore 3, which according to FIG. 2 runs obliquely, serves for receiving a transmitter 4 for a radiation that is intended according to the invention to impinge on smoke occurring, for example in a room. The transmitter 4 is assigned here a receiver 5, which is likewise located in a further oblique bore 6, which is aligned such that it impinges on the radiation of the transmitter 4 at a predetermined point and detects this radiation. At the instant at which it does not detect the radiation from the transmitter 4, this is a sign that there is smoke in the room, which scatters or conceals the radiation from the transmitter 4. At this instant, an alarm can be set off.

According to the invention, this smoke detector R is then assigned a further monitored region 11, in which, in particular, any movements or the surroundings of the smoke detector itself are monitored. This monitored region is in the broadest sense occupied by a movement detector. For this purpose, a monitoring transmitter 7 is located in a further opening 8 in the end plate 1, which is formed at least partially in the shape of a funnel.

In the preferred exemplary embodiment, it has a cylindrical region 9 for receiving the monitoring transmitter 7 and an adjoining funnel-shaped region 10, this funnel-shaped region 10 resembling an ellipse in cross section. This provides the possibility of widening the radiation emitted from the monitoring transmitter 7, so that a monitoring region 11 in the form of a sheet is produced. This is indicated by dashed lines. The monitoring region 11 is monitored by a monitoring receiver, preferably by two monitoring receivers 12.1 and 12.2, which can see this monitoring region 11 through further openings 13.1 and 13.2, respectively, in the end plate 1.

The receivers 12.1, 12.2, the monitoring transmitter 7 and also the receiver 5 and the transmitter 4 are located on a control plate 14, which is occupied by the corresponding electronic control units and components.

In this monitored region, any movements can be detected. This has the effect in particular that false alarms by the smoke detector are avoided by appropriate matching of the transmitter/receiver to the monitoring transmitter/monitoring receiver. Interference signals that are produced by insects or instances of soiling on the surface of the end plate 1 can be directly detected and evaluated and passed on as a fault message. Priorities are preferably set in the evaluation, which is very helpful in particular in clean rooms, in which fluff is often statically attracted to the end plate 1.

The invention claimed is:

1. An apparatus for detecting smoke and movement in a room, comprising:
- a smoke transmitter for transmitting a beam which is reflectable by smoke in a room;
- a smoke receiver which detects the beam reflected by smoke in the room;
- a monitoring transmitter for signaling movement of an object in the room;
- at least one monitoring receiver for receiving the movement signal of the object; and
- a control plate and an end plate spaced from the control plate, the smoke transmitter and receiver as well as the monitoring transmitter and monitoring receiver are located on the control plate, and the end plate is provided with (1) two oblique bores associated with the smoke transmitter and receiver, respectively, (2) a funnel-shaped opening associated with the monitoring transmitter, and (3) at least one further opening associated with the at least one monitoring receiver.

* * * * *